United States Patent

Nakano et al.

Patent Number: 5,424,832
Date of Patent: Jun. 13, 1995

[54] FLAMELESS ATOMIC ABSORPTION SPECTROPHOTOMETER

[75] Inventors: Tomohiro Nakano; Gen Taguchi, both of Kyoto, Japan

[73] Assignee: Shimadzu Corporation, Kyoto, Japan

[21] Appl. No.: 116,695

[22] Filed: Sep. 7, 1993

[30] Foreign Application Priority Data

Sep. 11, 1992 [JP] Japan ................................. 4-269498
Jan. 26, 1993 [JP] Japan ................................. 5-010464

[51] Int. Cl.$^6$ .......................... G01J 3/30; G01N 21/74
[52] U.S. Cl. ............................................................ 356/312
[58] Field of Search .......................................... 356/312

[56] References Cited

U.S. PATENT DOCUMENTS 4,660,976  4/1987  Falk ...................................... 356/312

FOREIGN PATENT DOCUMENTS

390072A1   3/1990   European Pat. Off. .
2222914   12/1973   France .
56-6143    1/1981   Japan ................................. 356/312
58-41338(A) 3/1983  Japan .
1461807    3/1974   United Kingdom .

Primary Examiner—Vincent P. McGraw
Assistant Examiner—K. P. Hantis
Attorney, Agent, or Firm—Oliff & Berridge

[57] ABSTRACT

A flameless atomic absorption spectrophotometer including a valve controller that connects the inside of the heating tube to the inert gas source before the sample is atomized, whereby water vapor or organic vapor generated from the sample before the atomizing stage is expelled from the tube through the sampling hole. In the atomizing stage of the heating program, the valve controller connects the inside of the heating tube to the outer atmosphere, whereby the atomized sample can expand along the optical path within the heating tube.

13 Claims, 8 Drawing Sheets

Fig.7A     Fig.7B
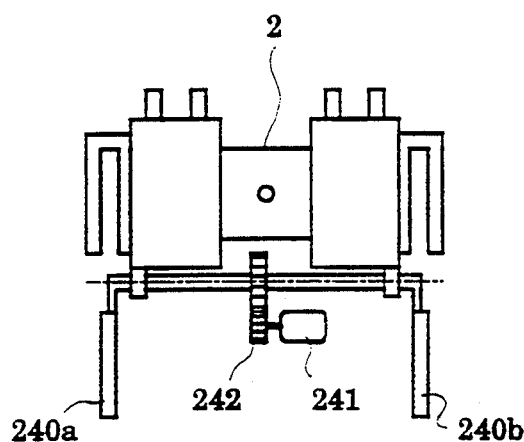
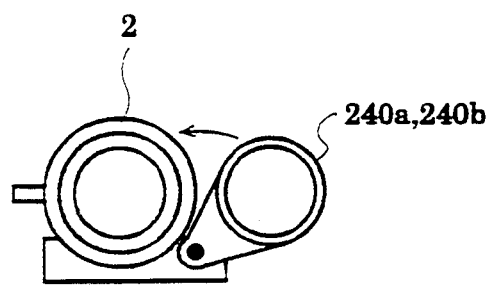
Fig. 8
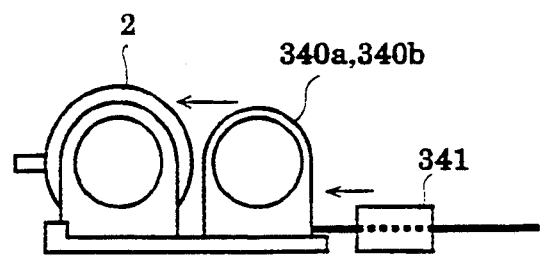

FLAMELESS ATOMIC ABSORPTION SPECTROPHOTOMETER

The present invention relates to a flameless atomic absorption spectrophotometer which uses a heating tube for atomizing the sample, and a method for using it.

BACKGROUND OF THE INVENTION

In measuring the content of an object element or elements in a sample with a flameless atomic absorption spectrophotometer, a known amount of sample is put in a heating tube (often a graphite tube is used), and the tube is heated to a high temperature to atomize the sample. A light is passed through a cloud of the atomized sample and the absorbing ratio (or the transmissivity) of the light at a specific wavelength or wavelengths corresponding to the object element is measured.

When metallic element or elements of a sample is measured and the sample includes water or organic component, the water or organic component is also vaporized in heating the tube and their vapors interfere with the absorption measurement of the object metallic element or elements. In order to avoid the interference, the heating program as shown in FIG. 1 (top) is used. First, the tube is heated at about 100° C. for several tens of seconds to vaporize the water content of the sample (drying). Then the tube is heated at 100°–1000° C. for several tens of seconds to vaporize the organic content of the sample (burning). After the water and organic contents are thus removed, the tube is heated to a proper high temperature (1000°–3000° C.) to atomize the object component (mainly metallic elements), on which the absorbing ratio is measured. The time needed to atomize the object component is several seconds.

In the drying and burning stages of the heating program, as shown in FIG. 9, a cloud 84 of water vapor or organic vapor is generated in the tube 81. Though some part of the cloud 84 goes out of the tube 81 through the small sampling hole 82 at the top of the tube 81, a large part of the cloud 84 expands along the optical path 83 toward the open ends of the tube 81 and lingers within the tube 81 until the atomizing stage. In a conventional flameless atomic absorption spectrophotometer, therefore, as shown in FIG. 10, a pair of transparent windows (often quartz plates) 95a and 95b are provided at the ends of electrodes 94a and 94b clamping and enclosing the tube 81, and inert gas (Ar gas, N$_2$ gas, etc.) is introduced within the tube 81 from the both ends of the tube 81 through passages (inner gas passages) 96a and 96b respectively provided at ends of the electrodes 94a and 94b. By such measures, the cloud 84 of water or organic vapor generated at the drying or burning stage is promptly expelled out of the tube 81 from the sampling holes 82 and 98 and the deleterious cloud 84 does not expand toward the ends of the tube 81. Another pair of passages (outer gas passages) 97a and 97b are provided in the electrodes 94a and 94b to introduce inert gas into the space between the tube 81 and the electrode envelope 94a and 94b in order to protect the graphite tube 81 from depletion by oxidization. The outer gas (gas introduced in the space between the tube 81 and the electrode envelope 94a and 94b) is drained from the gap between the two electrodes 94a and 94b.

A problem of the conventional flameless atomic absorption spectrophotometer is that a part of the atomized sample escapes through the sampling hole 82 to the outside of the tube 81 (or out of the optical path 83 of the measurement light). This is because the cloud of atomized sample cannot expand along the optical path 83 since the pressure within the tube 81 rises quickly at the atomizing stage and the ends of the optical path 83 (i.e., the ends of the electrode envelope 94a and 94b) are shut by the windows 95a and 95b.

Another problem of the conventional flameless atomic absorption spectrophotometer is that the windows 95a and 95b are not completely transparent to the measurement light and absorb some amount of light passing through the atomized sample. It is especially critical when the measurement uses light of shorter wavelength such as less than 200 nm. For example, 10% of the light is lost by a quartz window at the wavelength of $\lambda = 190$ nm. These problems lead to a poorer S/N ratio in the measurement.

SUMMARY OF THE INVENTION

An object of the present invention is therefore to provide an improved flameless atomic absorption spectrophotometer that prevents the atomized sample escaping from the heating tube.

Another object of the present invention is to eliminate the loss of the measurement light by the windows.

A method of measuring a content of an object element in a sample with a flameless atomic absorption spectrophotometer according to the present invention is as follows. In the flameless atomic absorption spectrophotometer, the heating tube has open ends and a sampling hole in the side wall. The method includes the following steps.

pre-heating the heating tube to a lower temperature before heating the sample at a high temperature to evaporate irrelevant components of the sample;

introducing an inert gas from the open ends and expelling the evaporated irrelevant components through the sampling hole out of the heating tube in the pre-heating step; and stopping the inert gas, and conducting the open ends of the heating tube to the outer atmosphere when the sample is atomized at the high temperature.

The method may further comprise the step of closing the sampling hole of the heating tube when the sample is atomized at the high temperature.

A flameless atomic absorption spectrophotometer according to the present invention comprises the following elements.

a heating tube for heating a sample, the heating tube having a sampling hole in a side wall;

a pair of end closing members each for enclosing an open end of the heating tube;

a pair of gas passages each provided in each of the end closing members for introducing an inert gas into the space within the heating tube;

a valve for connecting the gas passages either to an inert gas source or to an atmosphere;

a heating controller for heating the heating tube according to a preset heating program; and a valve controller for connecting the gas passages to the inert gas source before the sample is atomized in the heating tube and for connecting the gas passages to the atmosphere when the sample is atomized in the heating tube.

Before the sample is atomized, deleterious vapors in the heating tube are expelled by the inert gas through the sampling hole. When the sample is atomized, the atomized sample in the heating tube can expand within the heating tube.

The flameless atomic absorption spectrophotometer may further comprise the following elements.

a cap for closing a sampling hole provided in a side wall of the heating tube; and
   a cap controller for opening the sampling hole before the sample is atomized in the heating tube and for closing the sampling hole with the cap when the sample is atomized in the heating tube.

The capping in the atomizing stage enhances the expansion of the atomized sample within the heating tube.

Another flameless atomic absorption spectrophotometer according to the present invention includes the following elements.

a heating tube for heating a sample;
   a pair of end closing members each for enclosing an open end of the heating tube, each of the end enclosing members having an end hole at an end for passing light through the end holes and the heating tube;
   a pair of movable windows each for closing each of the end holes;
   a heating controller for heating the heating tube according to a preset heating program; and
   a window controller for closing the end holes with the windows before the sample is atomized in the heating tube and for opening the end holes when the sample is atomized in the heating tube.

Closing of the window before the atomizing stage helps to expel the deleterious vapors through the sampling hole. Opening of the window in the atomizing stage eliminates the loss of measurement light passing through the heating tube.

Other features and details of the present invention are fully disclosed in the following description of the preferred embodiments.

BRIEF DESCRIPTION OF THE DRAWINGS

FIG. 7A is a plan view of an atomizing section with another window moving mechanism, and FIG. 7B is the end view thereof.

FIG. 8 is an end view of an atomizing section with still another window moving mechanism.

DETAILED DESCRIPTION OF PREFERRED EMBODIMENTS

Figure 1:
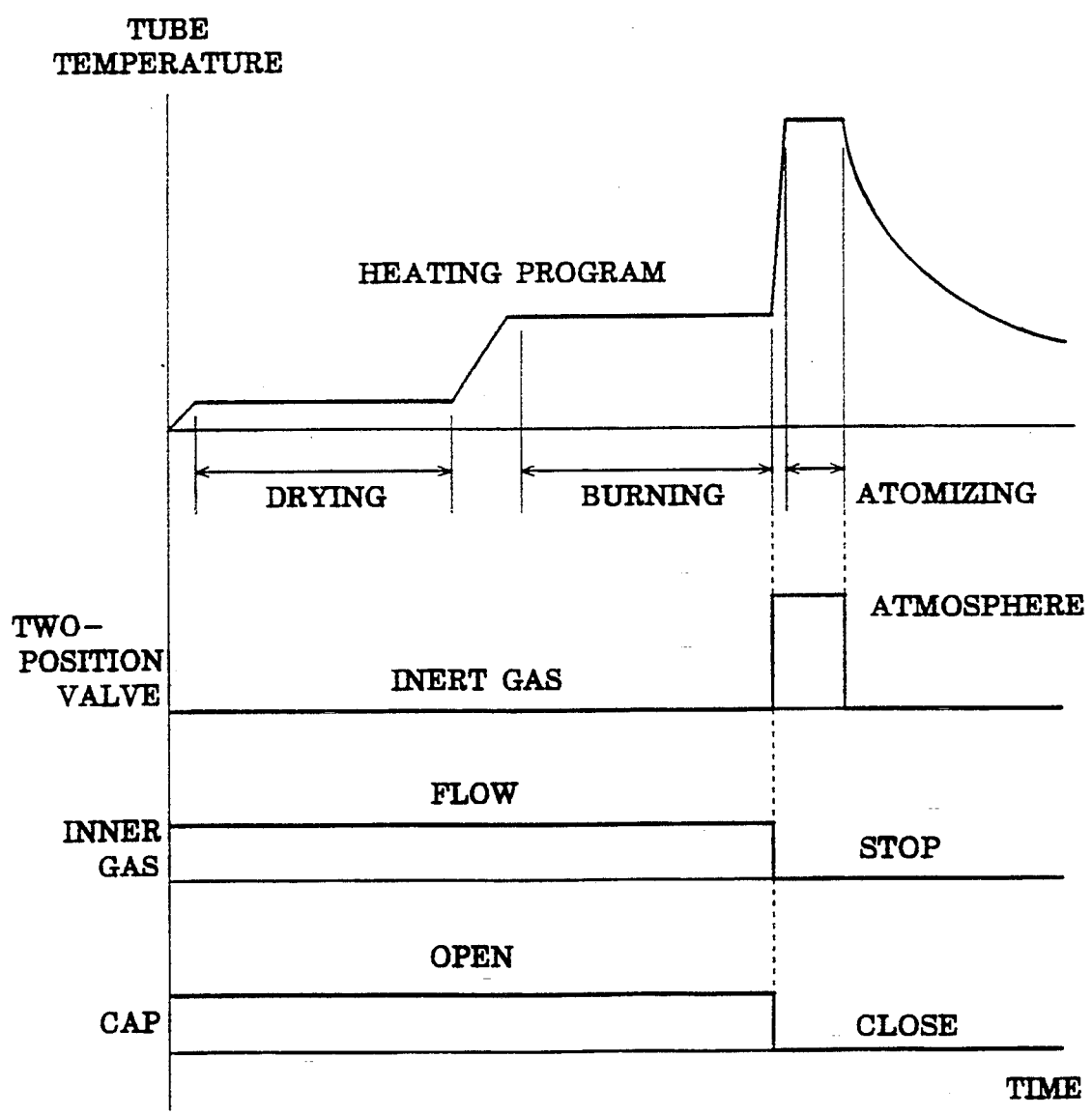
FIG. 1 is a time chart including a heating program, valve position, inner gas flow and a cap position.
Figure 2:
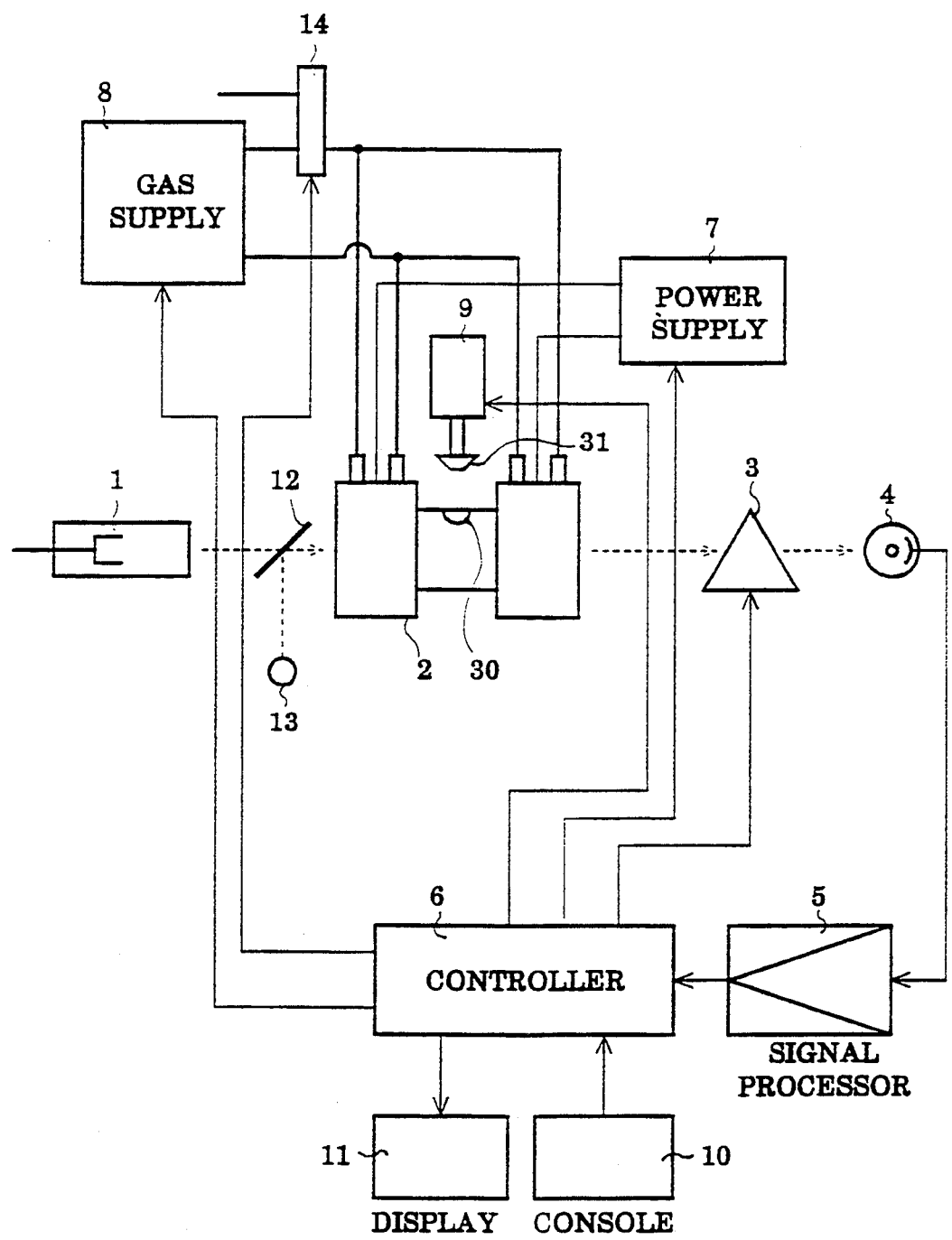
FIG. 2 is a construction diagram of a flameless atomic absorption spectrophotometer of the first embodiment of the present invention.
Figure 3:
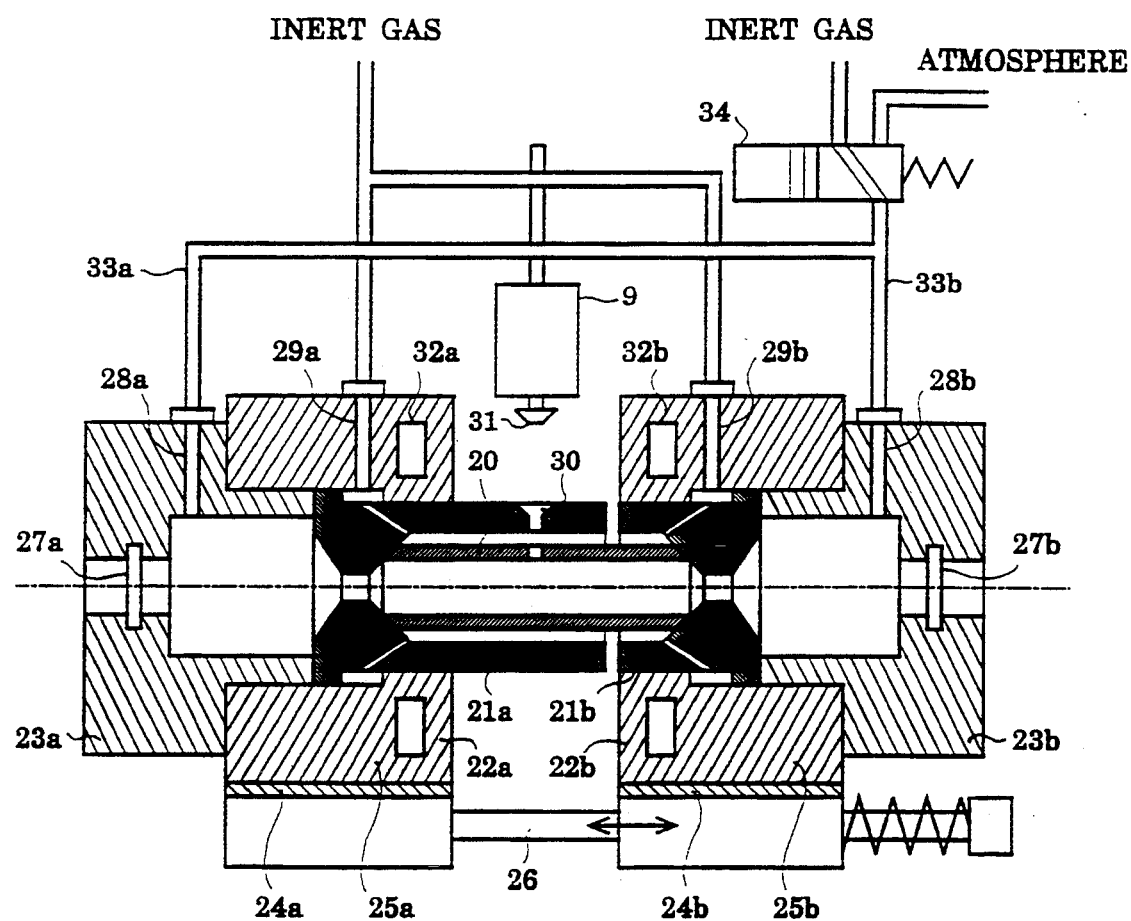
FIG. 3 is a cross sectional view of the atomizing section of the first embodiment.

The first embodiment of the present invention is explained referring to FIGS. 1 through 3. As shown in FIG. 2, a hollow cathode lamp 1 generates a bright line spectrum light including the resonance line of the object element or elements (the light is hereinafter referred to as the measurement light), and passes through a graphite tube 20 (FIG. 3) placed in an atomizing section 2, in which a sample is atomized and the object element in the atomized sample absorbs the resonance line of the measurement light. Then, irrelevant components of the measurement light (i.e., light that is not absorbed by the object element or light whose absorbing ratio is rather low) are separated and an object bright line (resonance line) is chosen by a light separator 3. The intensity of the chosen object bright line is measured by a detector 4. A half mirror 12 is placed before the atomizing section 2 in the optical path of the measurement light to pass the light from a deuterium ($D_2$) lamp 13 through the tube 20, too. The $D_2$ light is used to correct the background deviation in the measurement.

The signal from the detector 4 is converted logarithmically in a signal processor 5 and a signal corresponding to the absorbing ratio or a signal corresponding to the concentration of the object element is sent to a controller 6. The controller 6 sends the signal to a display 11 (CRT, LCD, etc.) to show the measurement result. A console (including a keyboard or a joystick) 10 is connected to the controller 6 to send directions to the controller 6.

In the atomizing section 2, as shown in FIG. 3, a graphite tube 20 is secured by a pair of graphite sleeves 21a and 21b (side closing members of the present invention), and the graphite sleeves 21a and 21b are held by a pair of copper electrode rings 22a and 22b. At the ends of electrode rings 22a and 22b are inserted a pair of plugs 23a and 23b (end closing members of the present invention). The sleeve 21a, the electrode ring 22a and the plug 23a are constructed as a unit, and another set 21b, 22b and 23b are also constructed as a unit. Each unit is supported by a substrate 25a or 25b via an insulating plate 24a or 24b, and the two units are made slidable in the direction of the optical path by a guide bar 26 penetrating through a substrate 25b, whereby the graphite tube 20 is replaceable.

When the graphite tube 20 is clamped by the two units, the electric power is given from a power supply 7 (FIG. 2) to the graphite tube 20 through the electrode rings 22a, 22b and the graphite sleeves 21a, 21b. A cooling water passage 32a or 32b is formed in each of the electrode rings 22a or 22b.

A quartz window 27a or 27b is tightly secured in each of the plugs 23a and 23b to enclose the space formed by the two plugs 23a and 23b and the sleeves 21a and 21b and to pass the measurement light.

A small hole (inner gas passage) 28a or 28b is formed in each plug 23a or 23b, and also a small hole (outer gas passage) 29a or 29b is formed in each electrode ring 22a and 22b. A through hole (sampling hole) 30 is formed in the side wall of the sleeve 21a and in the side wall of the graphite tube 20. The top of the sampling hole 30 is enlarged as shown in FIG. 3 and a cap 31 is provided for the sampling hole 30. The cap 31 is moved vertically (and preferably laterally) by a cap driver 9 to open and close the sampling hole 30.

A gas pipe (inner gas pipe) 33a or 33b is connected to the inner gas hole 28a or 28b, and another gas pipe (outer gas pipe) is connected to the outer gas hole 29a or 29b. The inner gas pipes 33a and 33b are joined and connected to a two-position valve 34. The two-position valve 34 connects the inner gas pipes 33a and 33b either to a gas supply 8 or to an outer atmosphere. The two-position valve 34 is driven by a valve changer 14 (FIG. 2).

The power supply 7, gas supply 8, valve changer 14 and cap driver 9 are electrically connected to the controller 6 and controlled by the controller 6 with the heating program as shown in FIG. 1. When an operator starts the system, the controller 6 controls the power supply 7 to heat the graphite tube 20 according to a preset heating program as shown at the top of FIG. 1. The heating program is given by the operator through the console 10 or previously stored in an external data storage or in a ROM (read only memory) provided to the controller 6. The power supply 7 supplies a large electric current through the electrode rings 22a, 22b and sleeves 21a, 21b to the graphite tube 20.

In the drying stage and in the burning stage of the heating program, the controller 6 sends a signal to the valve changer 14 to set the two-position valve 34 to connect the inner gas pipes 33a and 33b to the gas supply 8. The gas supply 8 is directed by the controller 6 to supply inert gas through the pipe, and the cap driver 9 is given a direction from the controller 6 to lift the cap 31 to open the sampling hole 30. By the gas flow configuration thus realized, inert gas is introduced through the inner gas passage 28a and 28b into the tube 20 from the open ends, whereby the cloud of water vapor or organic vapor generated from water component or organic component of the sample is expelled out of the tube 20 through the sampling hole 30. Thus, at the end of these stages, deleterious cloud of vapors constituting a background of absorbing ratio measurement is cleared from the inside of the tube 20. Inert gas is also supplied through the outer gas holes 29a and 29b to the space between the tube 20 and the sleeves 21a and 21b to prevent oxidization of the tube 20 in these stages.

Just before the atomizing stage, the controller controls the valve changer 14 to set the two-position valve 34 at the position to connect the inner gas pipes 33a and 33b to the atmosphere, and controls the cap driver 9 to drop the cap to close the sampling hole 30. Owing to the gas system thus realized, the ends of the tube 20 is conducted to the outer atmosphere through the outer gas holes 29a and 29b, and the cloud of atomized sample expands only toward the ends along the optical path. If the sampling hole 30 is very small, it is not absolute to cap the sampling hole 30 (and the cap driving mechanism is unnecessary). Since the measurement time (i.e., the time for measuring the light passing through the atomized sample) is generally very short, exhaustion of the atomized sample from the ends of the tube 20 is insignificant. The inert gas supply through the inner gas passages 29a and 29b is also stopped in this atomizing stage.

Figure 4:
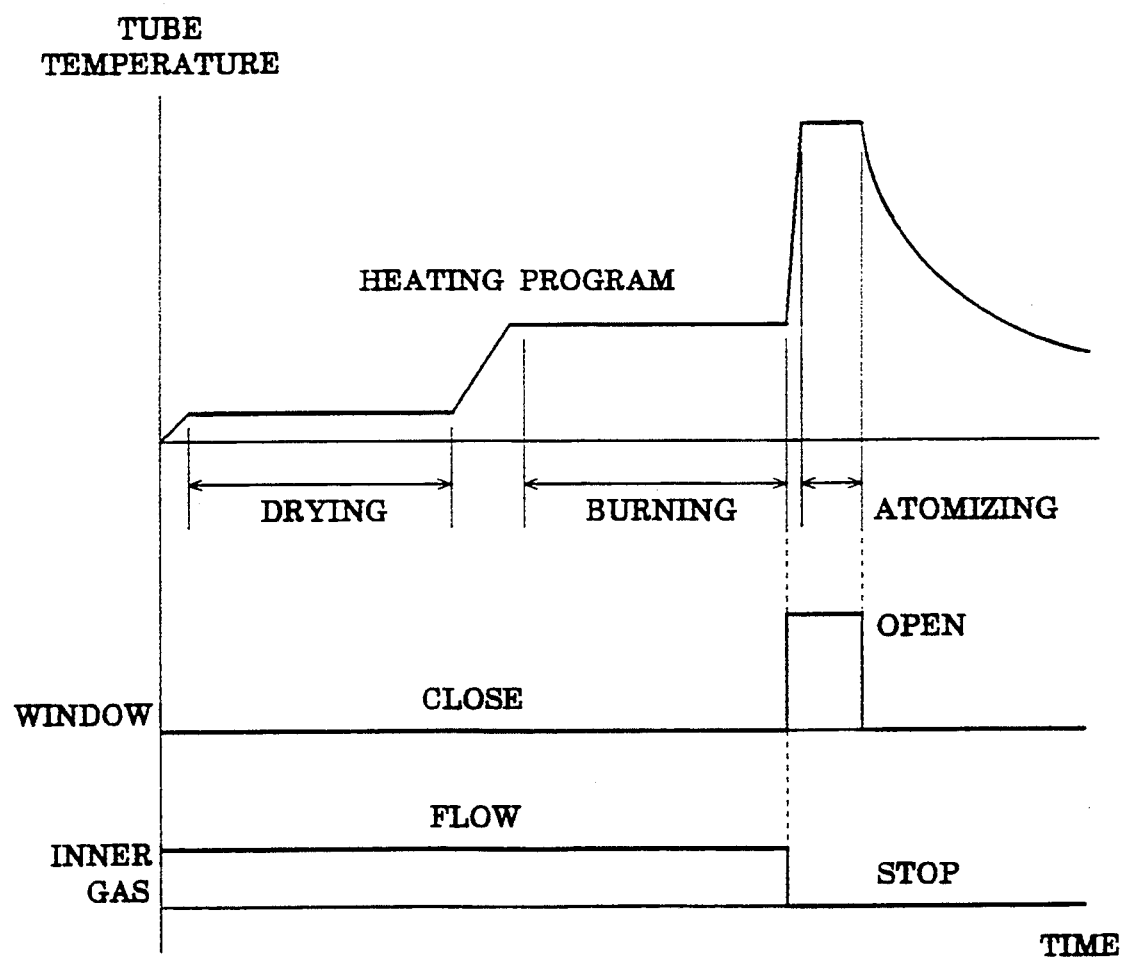
FIG. 4 is a time chart including a heating program, window position and an inner gas flow.
Figure 5:
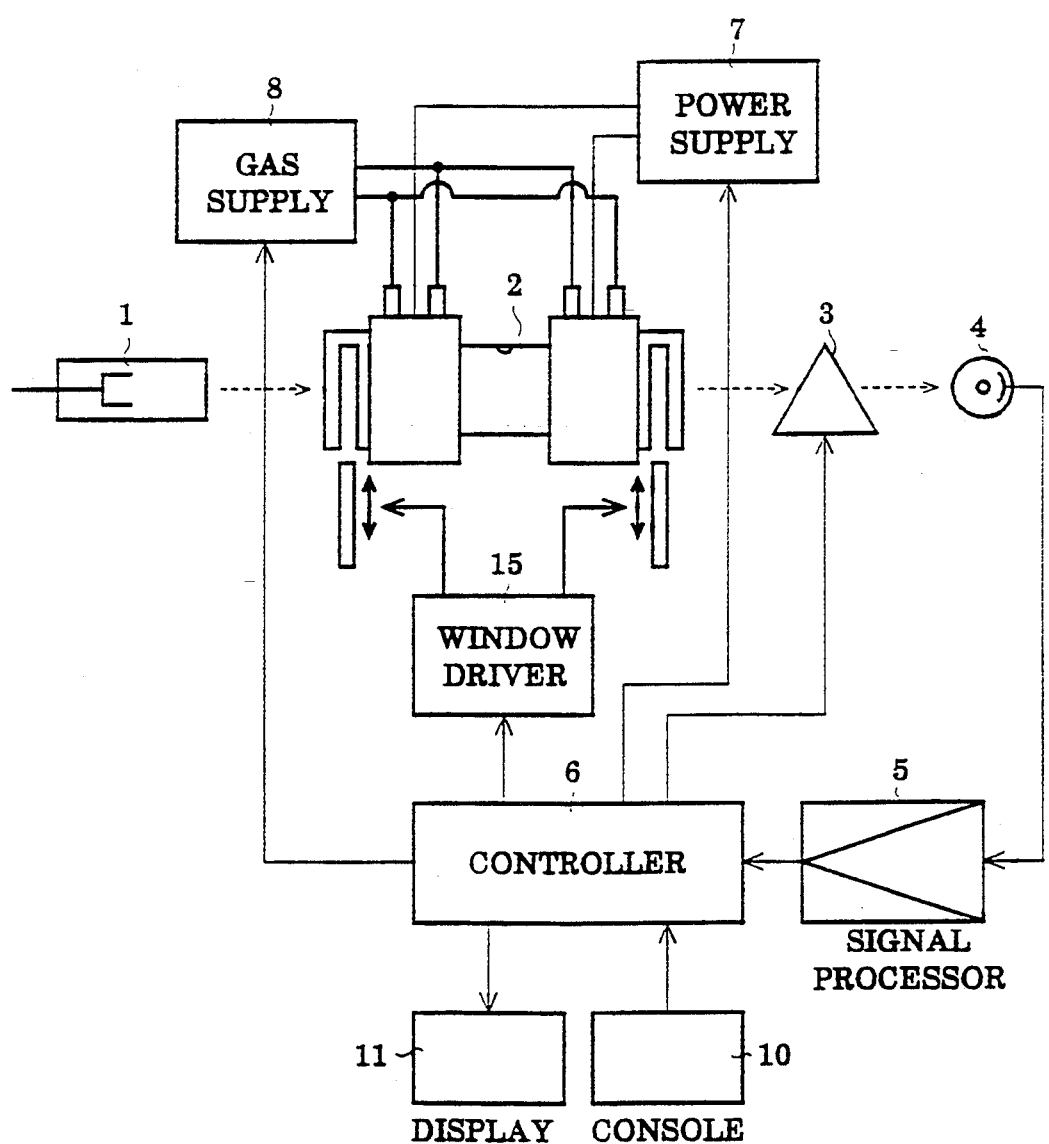
FIG. 5 is a construction diagram of a flameless atomic absorption spectrophotometer of the second embodiment of the present invention.
Figure 6:
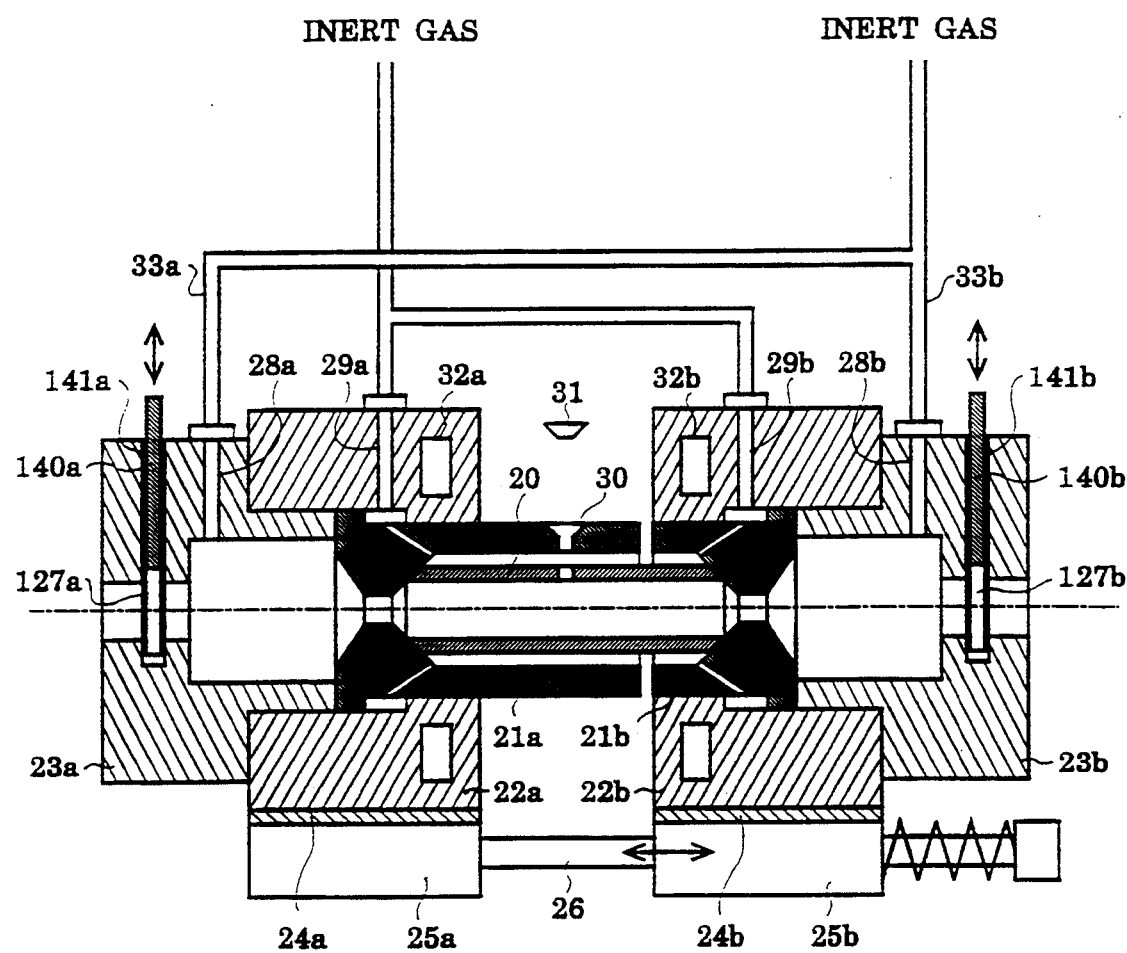
FIG. 6 is a cross sectional view of the atomizing section of the second embodiment.
Figure 9:
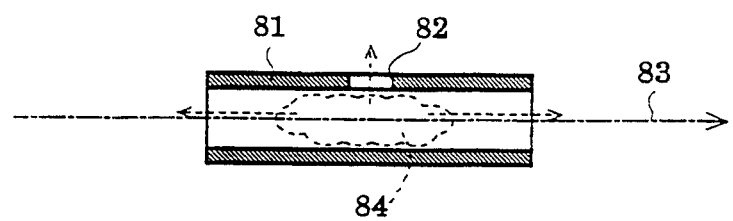
FIG. 9 is a cross sectional view of a heating tube.
Figure 10:
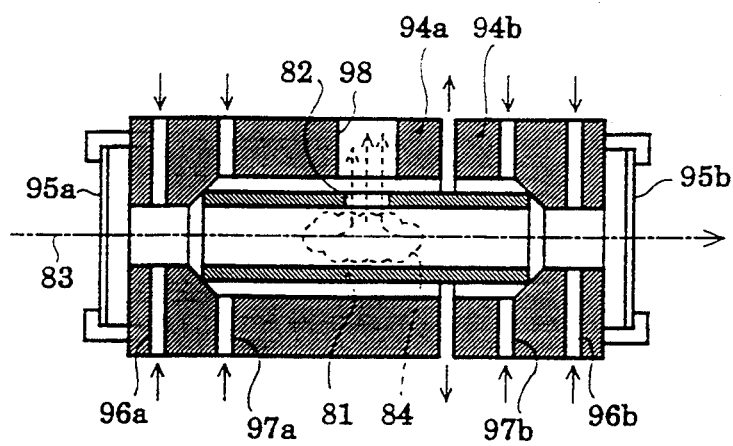
FIG. 10 is a cross sectional view of an atomizing section of a conventional flameless atomic absorption spectrophotometer.

The second embodiment of the present invention is explained referring to FIGS. 4 through 6. The basic structure of the system is the same as that of the previous embodiment, and the corresponding elements are numbered the same in FIGS. 2 and 3 and in FIGS. 5 and 6. The feature of the present embodiment is that the windows 27a and 27b fixed in the plugs 23a and 23b in the previous embodiment are made movable. In the present embodiment, a quartz window 127a or 127b is fixed to an end of a window holder 140a or 140b, and the window holder with the window is movably inserted in a slot 141a or 141b formed at the end of a plug 123a or 123b. As shown in FIG. 5, a window driver 15 is provided and connected to the controller 6 to slide the window holder 140a and 140b in the slots 141a and 141b to place the window 127a and 127b in the optical path or out of the optical path. No two-position valve is used in the present embodiment, and the outer gas pipes 33a and 33b are always connected to the gas supply 8.

In the present embodiment, the controller 6 controls the window driver 15 and the gas supply 8 as follows. When an operator starts the system, the controller 6 controls the power supply 7 to heat the graphite tube 20 according to a preset heating program as shown at the top of FIG. 4. The heating program is given by the operator through the console 11 or previously stored in an external data storage or in a ROM (read only memory) provided to the controller 6. The power supply 7 supplies a large electric current through the electrode rings 22a and 22b and sleeves 21a and 21b to the tube 20. In the drying and burning stages of the heating program, the controller 6 sends a signal to the window driver 15 to insert the windows 127a and 127b in the slot 141a and 141b to shut the space enclosed by the plugs 123a, 123b and the sleeves 21a, 21b. The controller 6 further sends a signal to the gas supply 8 to flow inert gas (Ar gas, $N_2$ gas, etc.) through the inner gas passages 28a and 28b into the enclosed space. The inert gas introduced in the tube 20 from the open ends expels the water vapor or organic vapor generated from the sample in the drying and burning stages out of the sampling hole 30. Thus, at the end of these stages, deleterious cloud of vapors constituting a background of absorbing ratio measurement is cleared from the inside of the tube 20. Inert gas is also supplied through the outer gas holes 29a and 29b to the space between the tube 20 and the sleeves 21a and 21b to prevent oxidization of the tube 20 in these stages.

Just before the atomizing stage begins, the controller 6 sends a signal to the window driver 15 to remove the window 127a and 127b from the optical path, and sends a signal to the gas supply 8 to stop the inert gas supply. With these measures, the cloud of atomized sample expands toward the ends of the tube 20, whereby more amount of atomized sample is involved in the absorbing ratio measurement. Further, no part of measurement light is lost by the windows 127a and 127b when the intensity of the light is measured by the detector 4. These enhances the sensitivity of the measurement which enables determination of less amount of object substance. The outer gas is continued to flow in this stage, too.

In the present embodiment, the windows 137a and 137b are removed from the optical path when the light passing on the optical path is measured, the window 137a and 137b need not be transparent. Though in the second embodiment, the cap is not moved according to the heating program, it is of course possible to adopt the same mechanism as in the previous embodiment to close the sampling hole 30 in the atomizing stage.

Some other structures of the window driver 15 are shown in FIGS. 6A through 7B. The mechanism shown in FIGS. 6A and 6B uses a motor 241 and gears 242 to rotate window holders 240a and 240b. The mechanism shown in FIGS. 7A and 7B uses a (electrical or pneumatic) pusher 341 to slide the window holders 340a and 340b.

What is claimed is:

1. A method of measuring a content of an object element in a sample with a flameless atomic absorption spectrophotometer in which the sample is atomized at a high temperature in a heating tube having a side wall and an intensity of a light passing through the atomized sample is measured, the heating tube having open ends and a sampling hole in the side wall, the method comprising the steps of:

pre-heating the heating tube to a temperature lower than the high temperature to evaporate irrelevant components of the sample;

introducing an inert gas into the open ends of the heating tube and expelling the evaporated irrelevant components out of the heating tube through the sampling hole;

stopping the introduction of the inert gas;

connecting the open ends of the heating tube to an outer atmosphere when the sample is atomized at the high temperature; and allowing the atomized sample to expand toward the open ends of the heating tube.

2. The flameless atomic absorption spectrophotometer measuring method according to claim 1, wherein the method further comprises the step of closing the sampling hole of the heating tube when the sample is atomized at the high temperature.

3. The flameless atomic absorption spectrophotometer measuring method according to claim 1, wherein a change valve connects the open ends of the heating tube to one of an inert gas source and the outer atmosphere.

4. The flameless atomic absorption spectrophotometer measuring method according to claim 1, where a pair of windows placed in the path of the light at the outside of the open ends of the heating tube are removed for connecting the open ends of the heating tube to the outer atmosphere.

5. A flameless atomic absorption spectrophotometer comprising:

a heating tube for heating a sample, the heating tube having a sampling hole in a side wall;

a pair of end closing members, each end closing member enclosing an open end of the heating tube;

a pair of gas passages, one as passage provided in each of the pair of end closing members for introducing an inert gas into a space within the heating tube;

a valve for connecting the pair of gas passages to one of an inert gas source and an outer atmosphere;

a heating controller for heating the heating tube according to a preset heating program; and a valve controller for connecting the gas passages to the inert gas source before atomizing the sample in the heating tube and for connecting the gas passages to the outer atmosphere when atomizing the sample in the heating tube to allow the atomized sample to expand toward the open ends of the heating tube.

6. The flameless atomic absorption spectrophotometer according to claim 5, further comprising:

a cap for closing the sampling hole of the heating tube and a cap controller for opening the sampling hole before atomizing the sample in the heating tube and for closing the sampling hole with the cap when atomizing the sample in the heating tube.

7. The flameless atomic absorption spectrophotometer according to claim 5, wherein a side closing member is provided around the heating tube to prevent oxidation of the heating tube by allowing the inert gas to flow between the side closing member and the heating tube, the side closing member having a hole corresponding to the sampling hole of the heating tube and a cap for closing the hole of the side closing member.

8. A flameless atomic absorption spectrophotometer comprising:

a heating tube for heating a sample having two open ends and a sampling hole in a side wall;

a pair of end closing members, each enclosing one open end of the heating tube, each of the end enclosing members having an end hole at an end for passing light through the end holes into the heating tube;

a pair of movable windows, each movable window closing one of the end holes;

a heating controller for heating the heating tube according to a preset heating program; and a window controller moving the movable windows to close the end holes before atomizing the sample in the heating tube and to open the end holes when atomizing the sample in the heating tube, to connect the open ends of the heating tube to an outer atmosphere and to allow the atomized sample to expand toward the open ends of the heating tube.

9. The flameless atomic absorption spectrophotometer according to claim 8, further comprising:

a cap for closing the sampling hole provided in the side wall of the heating tube; and a cap controller for opening the sampling hole before atomizing the sample in the heating tube and for closing the sampling hole with the cap when atomizing the sample in the heating tube.

10. The flameless atomic absorption spectrophotometer according to claim 8, wherein a side closing member is provided around the heating tube to prevent oxidation of the heating tube by allowing the inert gas to flow between the side closing member and the heating tube, the side closing member having a hole corresponding to the sampling hole of the heating tube and a cap for closing the hole of the side closing member.

11. The flameless atomic absorption spectrophotometer according to claim 8, further comprising:

a pair of gas passages, each gas passage provided in one of the end closing members;

an inert gas source for supplying an inert gas into the space within the heating tube through the gas passages; and a gas flow controller for supplying the inert gas from the inert gas source through the gas passages to the space within the heating tube before atomizing the sample in the heating tube and for stopping the inert gas when atomizing the sample in the heating tube.

12. The flameless atomic absorption spectrophotometer according to claim 11, further comprising:

a cap for closing the sampling hole provided in the side wall of the heating tube; and a cap controller for opening the sampling hole before atomizing the sample in the heating tube and for closing the sampling hole with the cap when atomizing the sample in the heating tube.

13. The flameless atomic absorption spectrophotometer according to claim 11, wherein a side closing member is provided around the heating tube to prevent oxidation of the heating tube by allowing the inert gas to flow between the side closing member and the heating tube, the side closing member having a hole corresponding to the sampling hole of the heating tube and a cap for closing the hole of the side closing member.

* * * * *